(12) United States Patent
Houser et al.

(10) Patent No.: US 8,540,742 B2
(45) Date of Patent: Sep. 24, 2013

(54) ULTRASONIC SURGICAL BLADE HAVING TRANSVERSE AND LONGITUDINAL VIBRATION

(75) Inventors: Kevin L. Houser, Springboro, OH (US); Laura A. Gallagher, Cincinnati, OH (US); Jean M. Beaupre, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 275 days.

(21) Appl. No.: 12/821,541

(22) Filed: Jun. 23, 2010

(65) Prior Publication Data
US 2010/0262172 A1   Oct. 14, 2010

Related U.S. Application Data

(63) Continuation of application No. 11/065,667, filed on Feb. 24, 2005, now abandoned.

(60) Provisional application No. 60/548,337, filed on Feb. 27, 2004.

(51) Int. Cl.
*A61B 17/32* (2006.01)

(52) U.S. Cl.
USPC ........................................................ 606/169

(58) Field of Classification Search
USPC ................ 600/437; 604/22; 601/2; 433/86, 433/119; 606/169
See application file for complete search history.

(56) References Cited

U.S. PATENT DOCUMENTS

| | | | |
|---|---|---|---|
| 3,817,141 A | 6/1974 | Simonetti | |
| 3,952,732 A | 4/1976 | Shock | |
| 4,989,588 A * | 2/1991 | Kubota et al. | 606/2 |
| 5,322,055 A | 6/1994 | Davison et al. | |
| 5,653,724 A | 8/1997 | Imonti | |
| 6,129,735 A | 10/2000 | Okada et al. | |
| 6,325,811 B1 | 12/2001 | Messerly | |
| 6,328,751 B1 * | 12/2001 | Beaupre | 606/169 |
| 6,652,547 B2 | 11/2003 | Rabiner et al. | |
| 2003/0236539 A1 | 12/2003 | Rabiner et al. | |

FOREIGN PATENT DOCUMENTS

WO     WO 03/095028 A1    11/2003

OTHER PUBLICATIONS

McCarus, Steven D., MD; Physiologic Mechanism of the Ultrasonically Activated Scalpel; Journal of the American Association of Gynecologic Laparoscopists; Aug. 1996; vol. 3 No. 4; 601ff.

Feil, Wolgang, MD, et al.; Ultrasonic Energy for Cutting, Coagulating and Dissecting; p. IV, 17, 21, 23; Theime; Stuttgart-New York 3-13-127521-9.

(Continued)

*Primary Examiner* — Ryan Severson
(74) *Attorney, Agent, or Firm* — Verne E. Kreger, Jr.

(57) ABSTRACT

An ultrasonic surgical blade includes an ultrasonic-surgical-blade body having a longitudinal axis, a distal tip, a proximal end adapted for longitudinal ultrasonic vibrational excitation, a most-distal longitudinal vibration node, a treatment portion extending from the distal tip toward the most-distal longitudinal vibration node, and a functional asymmetry. The functional asymmetry is asymmetric about the longitudinal axis and translates longitudinal ultrasonic vibrational movement of the proximal end into a combination of a longitudinal ultrasonic vibration and a transverse ultrasonic vibration in at least some of the treatment portion of the ultrasonic-surgical-blade body. An amplitude of the transverse ultrasonic vibration at the distal tip is less than substantially ten percent of a maximum amplitude of the transverse ultrasonic vibration of the treatment portion of the ultrasonic-surgical-blade body. An alternate embodiment of the ultrasonic surgical blade includes at least one functional asymmetry and at least one balance asymmetry.

12 Claims, 2 Drawing Sheets

(56) References Cited

OTHER PUBLICATIONS

International Search Report dated Jul. 20, 2011; International Application No. EP05724028.

Feil, Wolfgang, MD et al.; Ultrasonic Energy for Cutting, Coagulating, and Dissecting; p. IV, 17, 21, 23; ISBN 3-13-127521-9 (New York, NY, Thieme New York, 2005).

* cited by examiner

ULTRASONIC SURGICAL BLADE HAVING TRANSVERSE AND LONGITUDINAL VIBRATION

REFERENCE TO RELATED APPLICATIONS

The present application is a continuation of U.S. patent Ser. No. 11/065,667 filed Feb. 24, 2005 now abandoned which claims the priority benefit of U.S. provisional patent application Ser. No. 60/548,337, filed on Feb. 27, 2004, the contents of which are incorporated herein by reference.

FIELD OF THE INVENTION

The present invention is related generally to ultrasonic surgical instruments, and more particularly to an ultrasonic surgical blade.

BACKGROUND OF THE INVENTION

Ultrasonic surgical instruments are known which include ultrasonic surgical blades. A handpiece of a known ultrasonic surgical instrument includes an ultrasonic transducer which is powered by an ultrasonic generator through a cable. An ultrasonic transmission rod of the instrument has a first end and a second end. The first end of the ultrasonic transmission rod is operatively connected to the ultrasonic transducer. The second end of the ultrasonic transmission rod is connected to, or is an integral proximal extension of, an ultrasonic surgical blade. The ultrasonic surgical blade is activated by the ultrasonic transmission rod providing longitudinal ultrasonic vibration to the blade. Known blade shapes include straight blades and curved blades and include blades that are symmetric and blades that are asymmetric about a longitudinal axis or about a curved centerline of the blade. Known blades are designed to provide substantially purely longitudinal ultrasonic vibration along the blade. Exemplary devices are described in U.S. Pat. Nos. 5,322,055 and 6,325,811, the contents of which are incorporated herein by reference.

A known ultrasonic surgical blade is a cylindrical blade which has a distal tip, a most-distal vibration node (a vibration node being a point of substantially zero displacement), and a second most-distal vibration antinode (a vibration antinode being a point of maximum displacement relative to all other points in a half wave), wherein the most-distal vibration antinode is the distal tip. Longitudinal ultrasonic vibration of the blade generates motion and heat in the contacted tissue, wherein the heat primarily provides the means for the blade to cut and/or coagulate patient tissue.

The amplitude of the longitudinal ultrasonic vibration of a conventional ultrasonic surgical blade is zero at the most-distal vibration node and rises along a cosine curve to a maximum at the distal tip of the blade. Typically, an amplitude of at least 50% of the maximum amplitude is required for effective cutting, and the distance from the distal tip to such 50% point on the blade can be considered to be the effective cutting length of the blade. The blade is not considered useful beyond its effective cutting length. The effective cutting length is about 13 mm for a straight cylindrical titanium rod at a resonant frequency of about 55.5 kHz and an amplitude of at least 55 microns.

Still, scientists and engineers continue to seek improved ultrasonic surgical blades.

SUMMARY OF THE INVENTION

A first embodiment of an ultrasonic surgical blade of the invention includes an ultrasonic-surgical-blade body. The ultrasonic-surgical-blade body has a longitudinal axis, a distal tip, a proximal end adapted for longitudinal ultrasonic vibrational excitation, a most-distal longitudinal vibration node, a treatment portion extending from the distal tip toward the most-distal longitudinal vibration node, and a functional asymmetry. The functional asymmetry is asymmetric about the longitudinal axis and translates longitudinal ultrasonic vibrational movement of the proximal end into a combination of a longitudinal ultrasonic vibration and a transverse ultrasonic vibration in at least some of the treatment portion of the ultrasonic-surgical-blade body. An amplitude of the transverse ultrasonic vibration at the distal tip is less than substantially ten percent of a maximum amplitude of the transverse ultrasonic vibration of the treatment portion of the ultrasonic-surgical-blade body.

A first expression of a second embodiment of an ultrasonic surgical blade of the invention includes an ultrasonic-surgical-blade body. The ultrasonic-surgical-blade body has a distal tip, a proximal end adapted for longitudinal ultrasonic vibrational excitation, a most-distal longitudinal vibration node, a second-most-distal longitudinal vibration node, a treatment portion extending from the distal tip toward the second most-distal vibration node, at least one functional asymmetry, and at least one balance asymmetry. The at-least-one functional asymmetry and the at-least-one balance asymmetry create a balance point. Longitudinal ultrasonic vibrational movement of the proximal end creates ultrasonic vibration of the ultrasonic-surgical-blade body which is substantially purely longitudinal ultrasonic vibration proximal the balance point and which is a combination of longitudinal and transverse ultrasonic vibration distal the balance point and in at least some of the treatment portion. An amplitude of the transverse ultrasonic vibration at the distal tip is less than substantially ten percent of a maximum amplitude of the transverse ultrasonic vibration of the treatment portion of the ultrasonic-surgical-blade body.

A second expression of a second embodiment of an ultrasonic surgical blade of the invention includes an ultrasonic-surgical-blade body. The ultrasonic-surgical-blade body has a distal tip, a proximal end adapted for longitudinal ultrasonic vibrational excitation, a most-distal longitudinal vibration node, a second-most-distal longitudinal vibration node, a treatment portion extending from the distal tip toward the most-distal vibration node, at least one functional asymmetry, and at least one balance asymmetry. The at-least-one functional asymmetry and the at-least-one balance asymmetry create a balance point. The balance point is disposed between the most-distal longitudinal vibration node and the second-most-distal longitudinal vibration node. Longitudinal ultrasonic vibrational movement of the proximal end creates ultrasonic vibration of the ultrasonic-surgical-blade body which is substantially purely longitudinal ultrasonic vibration proximal the balance point and which is a combination of longitudinal and transverse ultrasonic vibration distal the balance point and in at least some of the treatment portion of the ultrasonic-surgical-blade body.

Several benefits and advantages are obtained from one or more of the embodiments and expressions of the invention. Applicants determined that the magnitude, and not the direction, of the ultrasonic vibration of an ultrasonic-surgical blade largely determined the effect of the blade on patient tissue. Applicants realized that transverse ultrasonic vibration of the treatment portion of the blade was beneficial which was contrary to conventional blade design which taught having substantially zero transverse vibration in the treatment portion of the blade. Applicants discovered that designing the ultrasonic-surgical-blade body to provide a combination of transverse and longitudinal ultrasonic vibration in at least some of the treatment portion of the ultrasonic-surgical-blade body yielded, in one example, a total ultrasonic vibration whose amplitude was larger, and more uniform, over a longer distance of the blade from the distal tip toward the most-distal longitudinal vibration node than would be achieved with a comparable blade conventionally designed to provide the treatment portion with substantially only longitudinal ultrasonic vibration. Also, an ultrasonic surgical blade can have a particular tissue effect, offering advantages for particular surgical applications, by designing a particular total (longitudinal and transverse) ultrasonic vibration amplitude versus distance (from the most-distal longitudinal vibration node) profile, as can be appreciated by those skilled in the art.

The present invention has, without limitation, application in robotic-assisted surgery.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, expressions, examples, etc. can be combined with any one or more of the other following-described embodiments, expressions, examples, etc.

Figure 1:
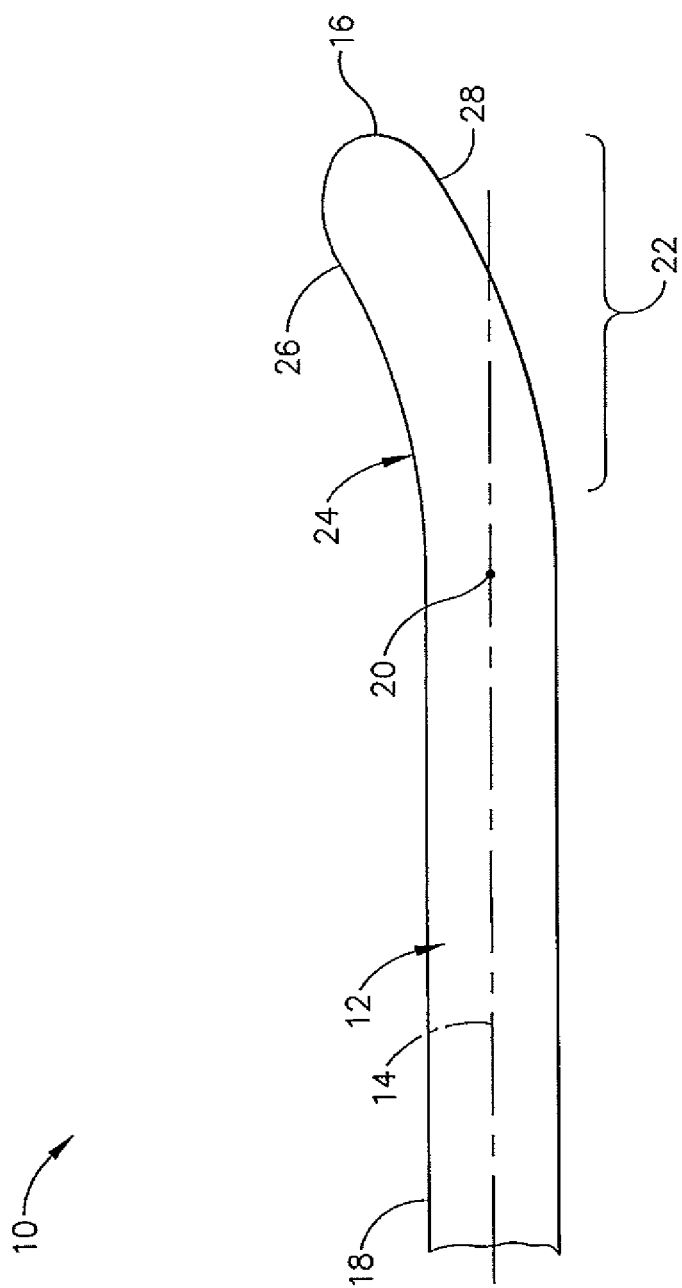
FIG. 1 is a schematic side view of a first embodiment of an ultrasonic surgical blade of the invention.

Referring now to the Figures, FIG. 1 illustrates a first embodiment of an ultrasonic surgical blade 10 of the invention. The ultrasonic surgical blade 10 includes an ultrasonic-surgical-blade body 12. The ultrasonic-surgical-blade body 12 has a longitudinal axis 14, a distal tip 16, a proximal end 18 adapted for longitudinal ultrasonic vibrational excitation, a most-distal longitudinal vibration node 20, a treatment portion 22 extending from the distal tip 16 toward the most-distal vibration node 20, and a functional asymmetry 24 which is asymmetric about the longitudinal axis 14 and which translates longitudinal ultrasonic vibrational movement of the proximal end 18 into a combination of a longitudinal ultrasonic vibration and a transverse ultrasonic vibration in at least some of the treatment portion 22 of the ultrasonic-surgical-blade body 12, wherein an amplitude of the transverse ultrasonic vibration at the distal tip 16 is less than substantially ten percent of a maximum amplitude of the transverse ultrasonic vibration of the treatment portion 22 of the ultrasonic-surgical-blade body 12.

For purposes of describing the invention, the treatment portion of the blade is that blade portion extending from the distal tip 16 toward the most-distal longitudinal vibration node 20 and having a vector sum amplitude of the amplitudes of the longitudinal and transverse ultrasonic vibrations of at least 50% of the maximum vector sum amplitude between and including the distal tip 16 and the most-distal longitudinal vibration node 20.

Functional asymmetries are described in U.S. Pat. No. 6,328,751 which is herein incorporated by reference. In one example of the embodiment of FIG. 1, the ultrasonic-surgical-blade body 12 has a curved shape distal the most-distal longitudinal vibration node 20, and the curved shape defines the functional asymmetry 24 of the ultrasonic-surgical-blade body 12. In one variation, the ultrasonic-surgical-blade body 12 has a concave-shaped top surface 26 and a convex-shaped bottom surface 28. In the same or another example, the ultrasonic-surgical-blade body 12 has at least two functional asymmetries.

In one enablement of the embodiment of FIG. 1, the functional asymmetry 24 is chosen and disposed to make the amplitude of the transverse ultrasonic vibration at the distal tip 16 substantially zero. In the same or a different enablement, the functional asymmetry 24 is chosen and disposed to make the vector sum amplitude of the amplitudes of the longitudinal and transverse ultrasonic vibrations, between the distal tip 16 and half way to the most-distal longitudinal vibration node 20, substantially equal to the amplitude of the longitudinal ultrasonic vibration at the distal tip 16. In the same or a different enablement, the functional asymmetry 24 is chosen and disposed to make the vector sum amplitude of the amplitudes of the longitudinal and transverse ultrasonic vibrations within plus or minus twenty-five percent of a particular value over at least half the distance between the most-distal longitudinal vibration node 20 and the distal tip 16. In one variation, the functional asymmetry 24 is chosen and disposed to make the vector sum amplitude of the amplitudes of the longitudinal and transverse ultrasonic vibrations within plus or minus ten percent of a particular value over at least half the distance between the most-distal longitudinal vibration node 20 and the distal tip 16. In the same or a different enablement, the functional asymmetry 24 is chosen and disposed to make the vector sum amplitude of the amplitudes of the longitudinal and transverse ultrasonic vibrations be above a predetermined value over a greater distance between the most-distal longitudinal vibration node 20 and the distal tip 16 than without the ultrasonic-surgical-blade body 12 having the functional asymmetry 24. In the same or a different enablement, the functional asymmetry 24 is chosen and disposed to make the vector sum amplitude of the amplitudes of the longitudinal and transverse ultrasonic vibrations substantially match a preselected profile of vector sum amplitude versus distance between the most-distal longitudinal vibration node 20 and the distal tip 16. Such choosing and disposing of functional asymmetries to accomplish the above-described results are within the level of skill of the artisan.

In one construction of the embodiment of FIG. 1, the ultrasonic-surgical-blade body 12 consists essentially of titanium. In other constructions, blade bodies consist essentially of aluminum, a ceramic, sapphire, or any other material that transmits ultrasound in an efficient manner. In one application, not shown, an ultrasonic transmission rod is an integral proximal extension of the proximal end 18 of the ultrasonic-surgical-blade body 12 and is longitudinally ultrasonically vibrated by an ultrasonic transducer powered by an ultrasonic generator through a cable.

In one implementation of the embodiment of FIG. 1, the maximum amplitude of the transverse ultrasonic vibration of the treatment portion 22 of the ultrasonic-surgical-blade body 12 is greater than substantially 50 percent of the maximum amplitude of the longitudinal ultrasonic vibration of the treatment portion 22. In one variation, the maximum amplitude of the transverse ultrasonic vibration of the treatment portion 22 is greater than substantially 90 percent of the maximum amplitude of the longitudinal ultrasonic vibration of the treatment portion 22. In the same or a different implementation, a point on the blade body 12 in the treatment portion 22 has an amplitude of transverse ultrasonic vibration which is greater than the amplitude of longitudinal ultrasonic vibration.

Figure 2:
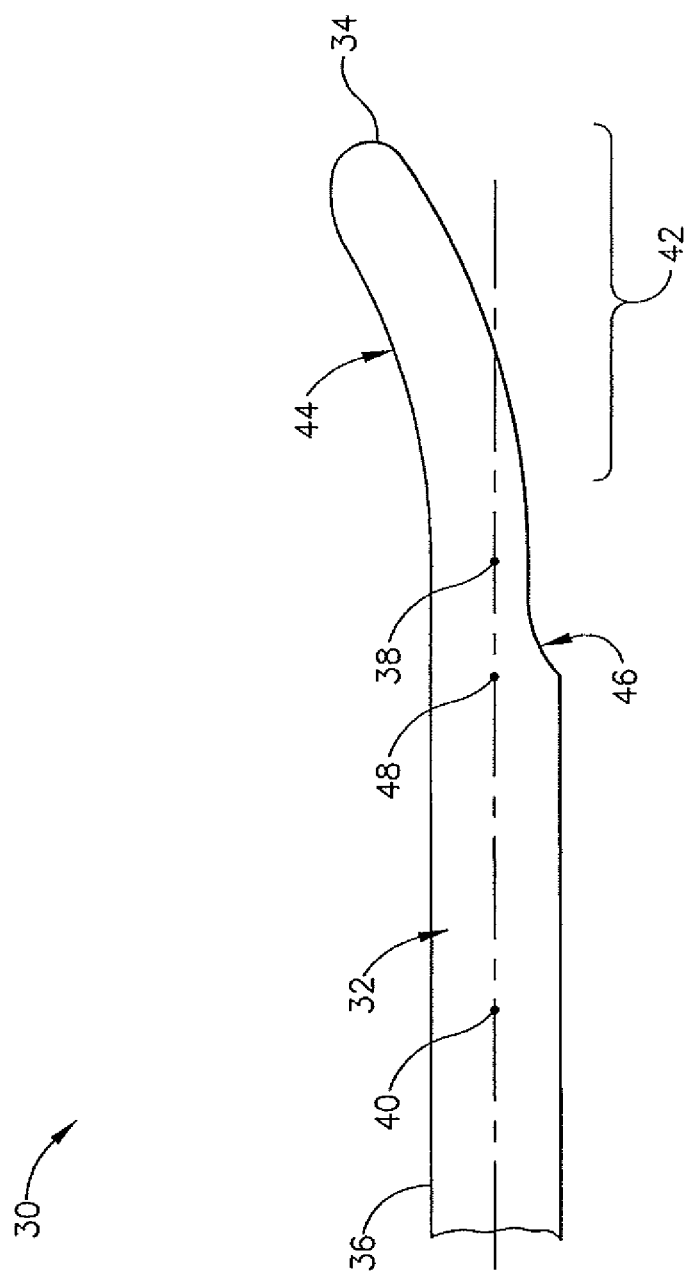
FIG. 2 is a schematic side view of a second embodiment of an ultrasonic surgical blade of the invention.

FIG. 2 illustrates a second embodiment of the invention. A first expression of the embodiment of FIG. 2 is for an ultrasonic surgical blade 30 having an ultrasonic-surgical-blade body 32. The ultrasonic-surgical-blade body 32 has a distal tip 34, a proximal end 36 adapted for longitudinal ultrasonic vibrational excitation, a most-distal longitudinal vibration node 38, a second-most-distal longitudinal vibration node 40, a treatment portion 42 extending from the distal tip 34 toward the second most-distal vibration node 40, at least one functional asymmetry 44, and at least one balance asymmetry 46. The at-least-one functional asymmetry 44 and the at-least-one balance asymmetry 46 create a balance point 48. Longitudinal ultrasonic vibrational movement of the proximal end 36 creates ultrasonic vibration of the ultrasonic-surgical-blade body 32 which is substantially purely longitudinal ultrasonic vibration proximal the balance point 48 and which is a combination of longitudinal and transverse ultrasonic vibration distal the balance point 48 and in at least some of the treatment portion 42. An amplitude of the transverse ultrasonic vibration at the distal tip 34 is less than substantially ten percent of a maximum amplitude of the transverse ultrasonic vibration of the treatment portion 42 of the ultrasonic-surgical-blade body 32.

Balance asymmetries are also described in U.S. Pat. No. 6,328,751 previously incorporated herein by reference. In one example of the first expression of the embodiment of FIG. 2, the at-least-one balance asymmetry 46 includes a cutout. In the same or a different example, the balance point 48 is disposed distal the second-most-distal longitudinal vibration node 40. In one variation, not shown, the balance point 48 is disposed distal the most-distal longitudinal vibration node 38. In the same or a different example, the ultrasonic-surgical-blade body 32 has a curved shape which defines the at-least-one functional asymmetry 44 of the ultrasonic-surgical-blade body 32, and the at-least-one balance asymmetry 46 includes a cutout in the ultrasonic-surgical-blade body 32.

In one enablement of the first expression of the embodiment of FIG. 2, the at-least-one functional asymmetry 44 and the at-least-one balance asymmetry 46 are chosen and disposed to make the vector sum amplitude of the amplitudes of the longitudinal and transverse ultrasonic vibrations within plus or minus twenty-five percent of a particular value over at least half the distance between the most-distal longitudinal vibration node 38 and the distal tip 34. In one variation, the at-least-one functional asymmetry 44 and the at-least-one balance asymmetry 46 are chosen and disposed to make the vector sum amplitude of the amplitudes of the longitudinal and transverse ultrasonic vibrations within plus or minus ten percent of a particular value over at least half the distance between the most-distal longitudinal vibration node 38 and the distal tip 34. In the same or a different enablement, the at-least-one functional asymmetry 44 and the at-least-one balance asymmetry 46 are chosen and disposed to make the vector sum amplitude of the amplitudes of the longitudinal and transverse ultrasonic vibrations be above a predetermined value over a greater distance between the most-distal longitudinal vibration node 38 and the distal tip 34 than without the ultrasonic-surgical-blade body 32 having the at-least-one functional asymmetry 44 and the at-least-one balance asymmetry 46. In the same or a different enablement, the at-least-one functional asymmetry 44 and the at-least-one balance asymmetry 46 are chosen and disposed to make the vector sum amplitude of the amplitudes of the longitudinal and transverse ultrasonic vibrations substantially match a preselected profile of vector sum amplitude versus distance between the most-distal longitudinal vibration node 38 and the distal tip 34. Such choosing and disposing of functional asymmetries 44 and balance asymmetries 46 to accomplish the above-described results are within the level of skill of the artisan.

A second expression of the embodiment of FIG. 2 is for an ultrasonic surgical blade 30 having an ultrasonic-surgical-blade body 32. The ultrasonic-surgical-blade body 32 has a distal tip 34, a proximal end 36 adapted for longitudinal ultrasonic vibrational excitation, a most-distal longitudinal vibration node 38, a second-most-distal longitudinal vibration node 40, a treatment portion 42 extending from the distal tip 34 toward the most-distal vibration node 38, at least one functional asymmetry 44, and at least one balance asymmetry 46. The at-least-one functional asymmetry 44 and the at-least-one balance asymmetry 46 create a balance point 48 which is disposed between the most-distal longitudinal vibration node 38 and the second-most-distal longitudinal vibration node 40. Longitudinal ultrasonic vibrational movement of the proximal end 36 creates ultrasonic vibration of the ultrasonic-surgical-blade body 32 which is substantially purely longitudinal ultrasonic vibration proximal the balance point 48 and which is a combination of longitudinal and transverse ultrasonic vibration distal the balance point 48 and in at least some of the treatment portion 42 of the ultrasonic-surgical-blade body 32.

In one example of the second expression of the embodiment of FIG. 2, the ultrasonic-surgical-blade body 32 has a curved shape distal the second-most-distal longitudinal vibration node 40, and the curved shape defines the at-least-one functional asymmetry 44 of the ultrasonic-surgical-blade body 32. In this example, the at-least-one balance asymmetry 46 includes a cutout in the ultrasonic-surgical-blade body 32. In one enablement of the second expression of the embodiment of FIG. 2, the at-least-one functional asymmetry 44 and the at-least-one balance asymmetry 46 are chosen and disposed to make the vector sum amplitude of the amplitudes of the longitudinal and transverse ultrasonic vibrations substantially match a preselected profile of vector sum amplitude versus distance between the second-most-distal longitudinal vibration node 40 and the distal tip 34.

Several benefits and advantages are obtained from one or more of the embodiments and expressions of the invention. Applicants determined that the magnitude, and not the direction, of the ultrasonic vibration of an ultrasonic-surgical blade largely determined the effect of the blade on patient tissue. Applicants realized that transverse ultrasonic vibration of the treatment portion of the blade was beneficial which was contrary to conventional blade design which taught having substantially zero transverse vibration in the treatment portion of the blade. Applicants discovered that designing the ultrasonic-surgical-blade body to provide a combination of transverse and longitudinal ultrasonic vibration in at least some of the treatment portion of the ultrasonic-surgical-blade body yielded, in one example, a total ultrasonic vibration whose amplitude was larger, and more uniform, over a longer distance of the blade from the distal tip toward the most-distal longitudinal vibration node than would be achieved with a comparable blade conventionally designed to provide the treatment portion with substantially only longitudinal ultrasonic vibration. Also, an ultrasonic surgical blade can have a particular tissue effect, offering advantages for particular surgical applications, by designing a particular total (longitudinal and transverse) ultrasonic vibration amplitude versus distance (from the most-distal longitudinal vibration node) profile, as can be appreciated by those skilled in the art.

The foregoing description of several embodiments and expressions of the invention has been presented for purposes of illustration. It is not intended to be exhaustive or to limit the invention to the precise forms disclosed, and obviously many modifications and variations are possible in light of the above teaching. For example, as would be apparent to those skilled in the art, the disclosures herein of the ultrasonic surgical blade have equal application in robotic assisted surgery taking into account the obvious modifications of such systems and components to be compatible with such a robotic system.

What is claimed is:

1. An ultrasonic surgical blade comprising an ultrasonic-surgical-blade body having a distal tip, a proximal end adapted for longitudinal ultrasonic vibrational excitation, a most-distal longitudinal vibration node, a second-most-distal longitudinal vibration node, a treatment portion extending from the distal tip toward the second most-distal vibration node, at least one functional asymmetry, and at least one balance asymmetry, wherein the at-least-one functional asymmetry and the at-least-one balance asymmetry create a balance point, wherein longitudinal ultrasonic vibrational movement of the proximal end creates ultrasonic vibration of the ultrasonic-surgical-blade body which is substantially purely longitudinal ultrasonic vibration proximal the balance point and which is a combination of longitudinal and transverse ultrasonic vibration distal the balance point and in at least some of the treatment portion, and wherein an amplitude of the transverse ultrasonic vibration at the distal tip is less than substantially ten percent of a maximum amplitude of the transverse ultrasonic vibration of the treatment portion of the ultrasonic-surgical-blade body.

2. The ultrasonic surgical blade of claim 1, wherein the ultrasonic-surgical-blade body has a curved shape which defines the at-least-one functional asymmetry of the ultrasonic-surgical blade body, and wherein the at-least-one balance asymmetry includes a cutout in the ultrasonic-surgical-blade body.

3. The ultrasonic surgical blade of claim 1, wherein the balance point is disposed distal the second-most-distal longitudinal vibration node.

4. The ultrasonic surgical blade of claim 3, wherein the balance point is disposed distal the most-distal longitudinal vibration node.

5. The ultrasonic surgical blade of claim 1, wherein the at-least-one functional asymmetry and the at-least-one balance asymmetry are chosen and disposed to make the vector sum amplitude of the amplitudes of the longitudinal and transverse ultrasonic vibrations within plus or minus twenty-five percent of a particular value over at least half the distance between the most-distal longitudinal vibration node and the distal tip.

6. The ultrasonic surgical blade of claim 5, wherein the at-least-one functional asymmetry and the at-least-one balance asymmetry are chosen and disposed to make the vector sum amplitude of the amplitudes of the longitudinal and transverse ultrasonic vibrations within plus or minus ten percent of a particular value over at least half the distance between the most-distal longitudinal vibration node and the distal tip.

7. The ultrasonic surgical blade of claim 5, wherein the at-least-one functional asymmetry and the at-least-one balance asymmetry are chosen and disposed to make the vector sum amplitude of the amplitudes of the longitudinal and transverse ultrasonic vibrations be above a predetermined value over a greater distance between the most-distal longitudinal vibration node and the distal tip than without the ultrasonic-surgical-blade body having the at-least-one functional asymmetry and the at-least-one balance asymmetry.

8. The ultrasonic surgical blade of claim 1, wherein the at-least-one functional asymmetry and the at-least-one balance asymmetry are chosen and disposed to make the vector sum amplitude of the amplitudes of the longitudinal and transverse ultrasonic vibrations be above a predetermined value over a greater distance between the most-distal longitudinal vibration node and the distal tip than without the ultrasonic-surgical-blade body having the at-least-one functional asymmetry and the at-least-one balance asymmetry.

9. The ultrasonic surgical blade of claim 1, wherein the at-least-one functional asymmetry and the at-least-one balance asymmetry are chosen and disposed to make the vector sum amplitude of the amplitudes of the longitudinal and transverse ultrasonic vibrations substantially match a preselected profile of vector sum amplitude versus distance between the most-distal longitudinal vibration node and the distal tip.

10. An ultrasonic surgical blade comprising an ultrasonic-surgical-blade body having a distal tip, a proximal end adapted for longitudinal ultrasonic vibrational excitation, a most-distal longitudinal vibration node, a second-most-distal longitudinal vibration node, a treatment portion extending from the distal tip toward the most-distal vibration node, at least one functional asymmetry, and at least one balance asymmetry, wherein the at-least-one functional asymmetry and the at-least-one balance asymmetry create a balance point which is disposed between the most-distal longitudinal vibration node and the second-most-distal longitudinal vibration node, and wherein longitudinal ultrasonic vibrational movement of the proximal end creates ultrasonic vibration of the ultrasonic-surgical-blade body which is substantially purely longitudinal ultrasonic vibration proximal the balance point and which is a combination of longitudinal and transverse ultrasonic vibration distal the balance point and in at least some of the treatment portion of the ultrasonic-surgical-blade body.

11. The ultrasonic surgical blade of claim 10, wherein the ultrasonic-surgical-blade body has a curved shape distal the second-most-distal longitudinal vibration node, wherein the curved shape defines the at-least-one functional asymmetry of the ultrasonic-surgical-blade body, and wherein the at-least-one balance asymmetry includes a cutout in the ultrasonic-surgical-blade body.

12. The ultrasonic surgical blade of claim 10, wherein the at-least-one functional asymmetry and the at-least-one balance asymmetry are chosen and disposed to make the vector sum amplitude of the amplitudes of the longitudinal and transverse ultrasonic vibrations substantially match a preselected profile of vector sum amplitude versus distance between the second-most-distal longitudinal vibration node and the distal tip.

* * * * *